United States Patent
Stevenson et al.

(10) Patent No.: US 6,946,422 B2
(45) Date of Patent: Sep. 20, 2005

(54) PREPARATION OF MIXED METAL OXIDE CATALYSTS FOR CATALYTIC OXIDATION OF OLEFINS TO UNSATURATED ALDEHYDES

(75) Inventors: Scott A. Stevenson, Houston, TX (US); Wugeng Liang, Katy, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 348 days.

(21) Appl. No.: 10/317,647

(22) Filed: Dec. 12, 2002

(65) Prior Publication Data

US 2004/0116284 A1 Jun. 17, 2004

(51) Int. Cl.[7] ............................ B01J 23/00; B01J 27/192; B01J 21/08; B01J 21/12; B01J 21/14
(52) U.S. Cl. ...................... 502/311; 502/212; 502/248; 502/249; 502/255; 502/305; 502/306; 502/316; 502/317; 502/321; 502/322
(58) Field of Search ................... 502/208, 212, 502/243, 248, 249, 252, 255, 305, 306, 311, 316, 317, 321, 322

(56) References Cited

U.S. PATENT DOCUMENTS

| | | | | |
|---|---|---|---|---|
| 3,907,713 A | * | 9/1975 | Grasselli et al. | 502/215 |
| 3,911,039 A | * | 10/1975 | Grasselli et al. | 585/626 |
| 3,984,477 A | * | 10/1976 | Kubo et al. | 568/479 |
| 4,065,468 A | * | 12/1977 | Grasselli et al. | 549/258 |
| 4,107,204 A | | 8/1978 | Murib | |
| 4,111,985 A | * | 9/1978 | Okada et al. | 562/546 |
| 4,156,660 A | * | 5/1979 | Grasselli et al. | 502/212 |
| 4,170,570 A | | 10/1979 | Zagata et al. | |
| 4,212,766 A | * | 7/1980 | Brazdil et al. | 502/205 |
| 4,213,917 A | * | 7/1980 | Dolhyj et al. | 558/416 |
| 4,511,671 A | | 4/1985 | Saito et al. | |
| 4,537,874 A | * | 8/1985 | Sato et al. | 502/311 |
| 4,556,731 A | * | 12/1985 | Guttmann et al. | 562/546 |
| 4,816,603 A | | 3/1989 | Oh-Kita et al. | |
| 4,849,539 A | | 7/1989 | Bergna | |
| 4,916,103 A | | 4/1990 | Martan et al. | |
| 4,918,214 A | | 4/1990 | Brazdil, Jr. et al. | |
| 4,925,823 A | * | 5/1990 | Krabetz et al. | 502/211 |
| 5,138,100 A | | 8/1992 | Matsuura | |
| 5,144,090 A | | 9/1992 | Honda et al. | |
| 5,166,119 A | | 11/1992 | Oh-Kita et al. | |
| 5,245,083 A | | 9/1993 | Matsuura | |
| 5,276,178 A | | 1/1994 | Onodera et al. | |
| 5,364,825 A | * | 11/1994 | Neumann et al. | 502/311 |
| 5,532,199 A | | 7/1996 | Watanabe et al. | |
| 5,602,280 A | | 2/1997 | Nagai et al. | |
| 5,658,842 A | * | 8/1997 | Midorikawa et al. | 502/314 |
| 5,663,113 A | * | 9/1997 | Midorikawa et al. | 502/314 |
| 5,677,261 A | * | 10/1997 | Tenten et al. | 502/439 |
| 5,686,373 A | * | 11/1997 | Tenten et al. | 502/312 |
| 5,688,739 A | * | 11/1997 | Drenski et al. | 502/308 |
| 5,856,259 A | | 1/1999 | Watanabe et al. | |
| 5,910,608 A | * | 6/1999 | Tenten et al. | 562/532 |
| 6,028,220 A | | 2/2000 | Wada et al. | |
| 6,043,184 A | | 3/2000 | Karmakar et al. | |
| 6,080,893 A | * | 6/2000 | Hecquet et al. | 568/479 |
| 6,383,976 B1 | * | 5/2002 | Arnold et al. | 502/311 |
| 6,384,275 B2 | * | 5/2002 | Lee et al. | 562/535 |
| 6,429,332 B1 | * | 8/2002 | Tanimoto et al. | 562/532 |
| 6,461,996 B2 | | 10/2002 | Chaturvedi et al. | |
| 6,596,897 B1 | * | 7/2003 | Guan et al. | 558/323 |
| 6,797,839 B1 | * | 9/2004 | Hibst et al. | 562/532 |

* cited by examiner

Primary Examiner—Cam N. Nguyen
(74) Attorney, Agent, or Firm—Jim Wheelington

(57) ABSTRACT

A process for making a catalyst containing oxides of molybdenum, bismuth, iron, cesium and, optionally, other metals, such as tungsten, cobalt, nickel, antimony, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium wherein metal compounds are dissolved and then precipitated as a catalyst precursor which is calcined to form a mixed metal oxide catalyst. The process of the present invention uses an organic acid, such as acetic acid, instead of nitric acid to dissolve the bismuth compound and, optionally, other metal compounds. The catalyst synthesized by this process may be used for the production of unsaturated aldehydes, such as methacrolein, by gas phase catalytic oxidation of olefins, such as isobutylene.

50 Claims, No Drawings

PREPARATION OF MIXED METAL OXIDE CATALYSTS FOR CATALYTIC OXIDATION OF OLEFINS TO UNSATURATED ALDEHYDES

BACKGROUND OF THE INVENTION

1. Field of the Invention

This invention relates to a process for synthesis of a mixed metal oxide catalyst containing oxides of molybdenum, bismuth, iron, cesium and, optionally, other metals for the production of unsaturated aldehydes from olefins, such as methacrolein by gas phase catalytic oxidation of isobutylene in the presence of air or another gas containing molecular oxygen.

2. Description of the Prior Art

Many catalysts have been disclosed for use in the production of acrolein or methacrolein by catalytic vapor phase oxidation of propylene or isobutylene. U.S. Pat. No. 4,170,570 discloses a catalyst for production of unsaturated carboxylic acids and anhydrides containing molybdenum; at least one of tin, copper germanium, antimony, bismuth, tellurium, manganese, arsenic, alkali metals, iron, magnesium, zinc and/or nickel; at least one of tungsten or chromium; and at least one of vanadium, phosphorus, antimony or cobalt. The catalyst was prepared by dissolving oxides of the metal components in distilled water and refluxing the mixtures until a dry catalyst was obtained.

U.S. Pat. No. 4,511,671 discloses a catalyst for manufacturing methacrolein containing molybdenum, tungsten, bismuth, iron; at least one of nickel and/or cobalt; at least one of alkali metals, alkaline earth metals and/or thallium; at least one of phosphorus, tellurium, antimony, tin, cerium, lead, niobium, manganese and/or zinc; and silicon, aluminum, zirconium, and/or titanium. Nitric acid was used to dissolve metal nitrates.

U.S. Pat. No. 4,816,603 discloses a catalyst for production of methacrolein and methacrylic acid containing molybdenum, tungsten, bismuth, iron, nickel, antimony, at least one of potassium, rubidium, and/or cesium, at least one of phosphorus, boron, sulfur, silicon, selenium and/or germanium, at least one of zinc and/or lead and at least one of magnesium, cobalt, manganese and/or tin. Nitric acid was used to dissolve metal nitrates.

U.S. Pat. No. 4,916,103 discloses a catalyst for oxidation of propylene to acrolein and acrylic acid containing molybdenum, bismuth, iron, cobalt or nickel, phosphorus; at least one of arsenic, antimony, tin, thallium, tungsten, an alkaline earth metal, zinc and/or chromium; and at least one of sodium, potassium, rubidium, cesium and/or indium. Nitric acid was used to dissolve metal nitrates.

U.S. Pat. No. 5,138,100 discloses a catalyst for preparing methacrolein with composition (1) of the formula:

$$Mo_aBi_bFe_cX_dY_eZ_fO_g$$

where X is at least one of Ni and Co, Y is at least one of K, Rb, Cs and Tl, Z is at least one of the elements belonging to Groups 2, 3, 4, 5, 6, 7, 11, 12, 13, 14, 15 and 16, specifically beryllium, magnesium, calcium, strontium, barium, titanium, zirconium, cerium, niobium, chromium, tungsten, manganese, copper, silver, zinc, cadmium, boron, aluminum, germanium, tin, lead, phosphorus, arsenic, antimony, sulfur, selenium and tellurium, a is 12, b is 0.1 to 10, c is 0 to 20, d is 0 to 20, e is 0 to 2, f is 0 to 4, and g satisfies the valence requirement and composition (2) of the formula:

$$Ln_hMo_aO_j$$

where Ln is at least one of the rare earth elements, h is 0.2 to 1.5, i is 1 and j satisfies the valence requirement. Nitric acid was used to dissolve metal nitrates.

U.S. Pat. No. 5,144,090 discloses a catalyst for preparing acrolein or methacrolein containing molybdenum, bismuth, iron; at least one of nickel and/or cobalt; and at least one of potassium, rubidium, cesium, titanium, zirconium, niobium, chromium, tungsten, manganese, copper, silver, zinc, cadmium, boron, aluminum, silicon, germanium, tin, lead, phosphorus, arsenic, antimony, silicon, selenium and/or tellurium. Nitric acid was used to dissolve bismuth nitrate.

U.S. Pat. No. 5,166,119 discloses a catalyst for producing methacrolein and methacrylic acid containing molybdenum, tungsten, bismuth, iron, antimony; at least one of nickel and/or cobalt; at least one of cesium and/or thallium; at least one of magnesium, manganese, zinc, barium and/or chromium; and at least one of phosphorus, boron, sulfur, silicon, cerium, potassium and/or rubidium. Nitric acid was used to dissolve metal nitrates and it was disclosed that the amount of nitric acid outside a certain range lowered the activity of the catalyst.

U.S. Pat. No. 5,245,083 discloses a catalyst for preparing methacrolein containing a first composition of molybdenum, bismuth, iron; at least one of nickel and/or cobalt; at least one of tungsten, beryllium, magnesium, sulfur, calcium, strontium, barium, tellurium, selenium, cerium, germanium, manganese, zinc, chromium, silver, antimony, lead, arsenic, boron, phosphorus, niobium, copper, tin, aluminum, zirconium and/or titanium mixed with a second composition of molybdenum and at least one of potassium, rubidium and cesium. Nitric acid was used to dissolve bismuth nitrate.

U.S. Pat. No. 5,276,178 discloses a catalyst for producing methacrolein and methacrylic acid containing molybdenum, tungsten, bismuth, iron; at least one of nickel and/or cobalt; at least one of alkali metal and/or thallium; at least one of alkaline earth metals; at least one of phosphorus, tellurium, antimony, tin, cerium, lead, niobium, manganese, arsenic and/or zinc; and at least one of silicon, aluminum, titanium and/or zirconium. Nitric acid was used to dissolve bismuth nitrate.

U.S. Pat. No. 5,532,199 discloses a catalyst for producing acrolein and acrylic acid or methacrolein and methacrylic acid containing molybdenum, bismuth, iron; at least one of nickel and/or cobalt; at least one of magnesium, zinc, manganese, tin and/or lead; at least one of phosphorus, boron, sulfur, tellurium, silicon, selenium, germanium, cerium, niobium, aluminum, titanium, zirconium, tungsten and/or antimony; and at least one of potassium, sodium, rubidium, cesium and/or thallium. Nitric acid was used to dissolve metal nitrates.

U.S. Pat. No. 5,602,280 discloses a catalyst for producing acrolein and acrylic acid or methacrolein and methacrylic acid containing molybdenum, bismuth, iron; at least one of nickel and/or cobalt; at least one of manganese, zinc calcium, magnesium, tin and/or lead; at least one of phosphorus, boron, arsenic, tellurium, tungsten, antimony and/or silicon; and at least one of potassium, rubidium, cesium and/or thallium. Nitric acid was used to dissolve bismuth nitrate.

U.S. Pat. No. 5,856,259 discloses a catalyst for producing methacrolein and methacrylic acid containing molybdenum, bismuth, iron; at least one of nickel and/or cobalt; at least one of magnesium, zinc, manganese, tin and/or lead; at least one of phosphorus, boron, sulfur, tellurium, silicon, germanium, cerium niobium, titanium, zirconium, tungsten and antimony; and at least one of potassium, sodium, rubidium, cesium and/or thallium. Nitric acid was used to dissolve metal nitrates.

U.S. Pat. No. 6,028,220 discloses a catalyst for producing acrolein and acrylic acid containing molybdenum, bismuth, nickel, cobalt, iron; at least one of tin, zinc, tungsten, chromium, manganese, magnesium, antimony and/or titanium; and at least one of potassium, rubidium, thallium and/or cesium. Nitric acid was used to dissolve bismuth nitrate.

Prior art discloses the use of nitric acid to dissolve metal nitrates, particularly bismuth nitrate, in the synthesis of catalysts for producing acrolein and acrylic acid or methacrolein and methacrylic acid. Use of nitric acids generates nitrate salts which can decompose violently during heating (calcination). Also, oxides of nitrogen are produced during calcination which is undesirable from an environmental standpoint.

U.S. Pat. No. 6,461,996 discloses acetic acid as a product of a process for selective oxidation of propane to acrylic acid, acrolein and acetic acid using a catalyst containing molybdenum, vanadium, gallium, palladium, niobium and at least one of lanthanum, tellurium, germanium, zinc, silicon, indium and/or tungsten.

U.S. Pat. No. 6,043,184 discloses a heteropoly acid for direct catalytic oxidation of alkanes to unsaturated carboxylic acids, specifically propane to acrylic acid. Acetic acid/water was used as a medium to mix sodium acetate, iron nitrate and nickel nitrate to prepare a trimetal acetate which was a reactant in the process to prepare the heteropoly acid. Acetic acid was also a reaction product of the oxidation of propane.

U.S. Pat. No. 4,918,214 discloses acetic acid and water as a solvent for the alumina support of a vanadium-phosphorus-tungsten catalyst for the ammoxidation of propane.

U.S. Pat. No. 4,107,204 discloses a three-step process for the oxidation of propylene to acrylic acid in the presence of a palladium catalyst and acetic acid.

U.S. Pat. No. 4,849,539 discloses dissolving indium metal in acetic acid and isobutyl alcohol in the preparation of a vanadium-phosphorus oxide catalyst precursor for the production of maleic anhydride from n-butane, oxygen and nitrogen.

SUMMARY OF THE INVENTION

The present invention is for a process of making a catalyst of the general formula:

$$Mo_{12}Bi_aFe_cCs_gO_x$$

wherein a is in the range from 0.1 to 1.5, c is in the range from 0.2 to 5.0, g is in the range from 0.1 to 1.5 and x is determined by the valences of the other components. The catalyst may contain other metals, such as tungsten, cobalt, nickel, antimony, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium. The process of the present invention uses a solvent which is not nitric acid for dissolving a bismuth compound, especially bismuth nitrate. A bismuth compound is dissolved in an organic acid to form a solution or slurry. Preferably, the organic acid is of the general formula RCOOH or HOOCR'$_n$COOH where R is an alkyl group of one to six carbon atoms, an aryl group of six to ten carbon atoms, an alkylhydroxy group of one to six carbon atoms or an alkylhalide group of one to six carbon atoms and where R' is an alkyl group of one to six carbon atoms or an aryl group of six to ten carbon atoms and n is 1 or 0 indicating whether the R' group is present or not.

The bismuth compound is brought into contact with a molybdenum compound, an iron compound, a cesium compound and, optionally, compounds of other metals, such as tungsten, cobalt, nickel, antimony, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium. The contact with the bismuth compound may be subsequent to or simultaneous with the formation of the solution or slurry in the organic acid. Preferably, a first solution or slurry is formed with a molybdenum compound and, optionally, a tungsten compound and a phosphorus compound in water. A second solution or slurry is formed with a bismuth compound, an iron compound and, optionally, a nickel compound, a cobalt compound, a magnesium compound, a zinc compound, a potassium compound, a rubidium compound, a thallium compound, a manganese compound, a barium compound, a chromium compound, a boron compound, a sulfur compound, a silicon compound, an aluminum compound, a titanium compound, a cerium compound, a tellurium compound, a tin compound, a vanadium compound, a zirconium compound, a lead compound, a cadmium compound, a copper compound, and/or a niobium compound by dissolving with an organic acid, such as acetic acid. The second solution or slurry is added to the first solution or slurry. A cesium compound and, optionally, an antimony compound are added to the combined solution or slurry. It is preferable that the molybdenum compound and the tungsten compound are ammonium salts, that the phosphorus compound is phosphoric acid, and that the bismuth compound, the iron compound, the nickel compound, the cobalt compound, the magnesium compound, the zinc compound, the cesium compound, the potassium compound, the rubidium compound, the thallium compound, the manganese compound, the barium compound, the chromium compound, the boron compound, the sulfur compound, the silicon compound, the aluminum compound, the titanium compound, the cerium compound, the tellurium compound, the tin compound, the vanadium compound, the zirconium compound, the lead compound, the cadmium compound, the copper compound, and the niobium compound are nitrates, oxides or acids and the antimony compound is an oxide.

DESCRIPTION OF EMBODIMENTS OF THE INVENTION

According to the present invention, a process is provided for making a catalyst for producing acrolein or methacrolein by oxidation of propylene or isobutylene. The oxidation is a catalytic reaction that converts an olefin in the presence of oxygen to an unsaturated aldehyde and water:

$$H_2C=CA_x—CH_3+O_2 \rightarrow H_2C=CA_x—CHO+H_2O$$

where A is hydrogen or an alkyl group. Carboxylic acid is also produced in a side reaction.

The catalyst is a mixed metal oxide of the formula:

$$Mo_{12}Bi_aFe_cCs_gO_x$$

wherein a is in the range from 0.1 to 1.5, c is in the range from 0.2 to 5.0, g is in the range from 0.1 to 1.5 and x is determined by the valences of the other components. For a catalyst for oxidation of isobutylene to methacrolein, g preferably is in the range from 0.4 to 1.5. Preferably, the catalyst is of the formula:

$Mo_{12}Bi_aFe_cCs_gM_mO_x$ wherein M is selected from one or more of tungsten, cobalt, nickel, antimony, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium and m is in the range from 0 to 9. Most preferably, the catalyst is of the formula:

$Mo_{12}Bi_aW_bFe_cCo_dNi_eSb_fCs_gMg_hZn_iP_jO_x$ wherein b is 0 to 4, d is 0 to 9, e is 0 to 9, f is 0 to 2.0, g is 0.1 to 1.5, h is 0 to 1.5, i is 0 to 2.0 and j is 0 to 0.5 and the other variable are as defined above.

The process of making the catalyst is generally to dissolve the metal compounds and precipitate a catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. Preferably, the metal compounds are soluble in water or an organic acid. It is more preferred that the molybdenum compound and the tungsten compound are ammonium salts, such as ammonium paramolybdate or ammonium molybdate and ammonium paratungstate or ammonium tungstate, respectively, that the phosphorus compound is phosphoric acid, that the bismuth, iron, cobalt, nickel, cesium, magnesium, zinc, potassium, rubidium, thallium, manganese, barium, chromium, boron, sulfur, silicon, aluminum, titanium, cerium, tellurium, tin, vanadium, zirconium, lead, cadmium, copper and niobium compounds are nitrates, oxides or acids and that the antimony compound is an oxide, such as antimony oxide or antimony trioxide. For bismuth, iron, cesium, cobalt, nickel, magnesium and zinc compounds, it is preferred that they are nitrates.

The bismuth compound is dissolved in an organic acid. The other metal compounds may be dissolved in water or in the organic acid. The organic acid preferably is of the general formulae:

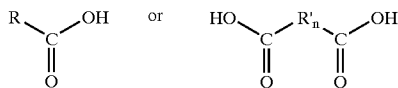

where R is an alkyl group of one to six carbon atoms, an aryl group of six to ten carbon atoms, an alkylhydroxy group of one to six carbon atoms or an alkylhalide group of one to six carbon atoms, R' is an alkyl group of one to six carbon atoms or an aryl group of six to ten carbon atoms and n is 1 or 0 indicating whether the R' group is present or not in the diacid. The organic acid is preferably acetic acid, formic acid, citric acid, oxalic acid, benzoic acid, phthalic acid, lactic acid, malonic acid, adipic acid or chloroacetic acid and, most preferably is acetic acid.

The present invention does not depend on a particular order of addition of the components. While a particular order of addition of the various metal compound components may affect the performance of the catalyst, the present invention is directed toward the use of an organic acid to dissolve the bismuth compound without regard to the order in which this step or other steps in the process of making the catalyst occur.

An example of the claimed invention is to dissolve an ammonium salt of molybdenum and, optionally, an ammonium salt of tungsten and phosphoric acid in water, dissolve a bismuth nitrate, in an organic acid, dissolve a iron nitrate and, optionally, a cobalt nitrate, a nickel nitrate, a magnesium nitrate and a zinc nitrate, in water or in the organic acid with the bismuth nitrate, mix the solutions to obtain a precipitate to form a slurry and then add a cesium nitrate and, optionally, an antimony oxide to the slurry. The cesium nitrate and the antimony oxide may be added to the slurry as solids. The slurry may be aged for 0 to 24 hours, preferably 8 to 18 hours, most preferably approximately 10 hours. The liquid of the slurry is removed by filtration, evaporation or centrifuge and the solid precipitate is dried and calcined to obtain a catalyst. The liquid may be removed and the solid precipitate dried at the same time by spray drying. The liquid may be evaporated at a temperature of 75° to 125° C.

Drying of the catalyst precursor may be in air or an inert gas and in an oven or a spray dryer. Preferably, drying is in an oven in air at a temperature of 100–150° C. for 2–5 hours Calcination of the catalyst precursor is to obtain an oxide of the metal components. The catalyst precursor may be calcined at a temperature of 200–600° C. for 1–12 hours. Preferably, calcination is in two stages, one at a temperature of 150–400° C. for 1–5 hours and another at a temperature of 460–600° C. for 4–8 hours. More preferably, the two-stage calcination is first at a temperature of 290–310° C. for 2 hours and second at a temperature of 460–500° C. for 6 hours. Calcination may be done in a high temperature oven or kiln.

The catalyst may be processed by sieving, forming and other means known in the art to obtain catalyst particles of a certain size. Desired particle size and particle size distribution is related to the design of the reactor (size, shape, configuration, etc.), on the pressure drop intended for the process and on the process flow. For a two stage calcination, the catalyst may be sieved or formed after the first stage calcination and before the second stage calcination. In a commercial process the catalyst precursor maybe be sieved and formed after spray drying and before calcination.

The X-ray diffraction pattern of the mixed metal oxide compounds is descriptive of the catalyst made by the process of the present invention. The catalyst compositions of the Examples above have a characteristic X-ray diffraction having substantial diffraction peaks at the diffraction angles of 2θ, measured by using Cu Kα radiation, at 25.5, 26.6, and 28.0 (+/−0.1°).

The catalyst of the present invention may be used as an unsupported catalyst or a supported catalyst. The surface area of an unsupported catalyst is from 0.1 to 150 m²/g, preferably from 1 to 20 m²/g. If supported, the support should be an inert solid which is chemically unreactive with any of the active components of the catalyst and is preferably silica, alumina, niobia, titania, zirconia or mixtures thereof. The catalyst may be affixed to the support by methods known in the art, including incipient wetness, slurried reactions and spray drying. The catalyst is not limited by shape, size or particle distribution and may be formed as appropriate for the reaction vessel in the process. Examples are powder, granules, spheres, cylinders, saddles, etc.

The catalyst may be used in the gas phase catalytic oxidation of a feedstock gas comprising propylene or isobutylene, oxygen, water and an inert gas, such as nitrogen, a hydrocarbon which is gaseous under the process conditions or carbon dioxide, to produce acrolein or methacrolein. Oxygen may be supplied in the pure form or in an oxygen-containing gas, such as air or a mixture of oxygen and a diluent gas. The diluent gas may be nitrogen, carbon dioxide or a mixture thereof. The reaction temperature is preferably from 250–450° C., most preferably 370–410° C. The reactor may be a fixed bed or a fluidized bed reactor. Reaction pressure may be from 0 to 100 psig. Space velocity may be from 800 to 8000 hr$^{-1}$.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

43.57 g of ammonium paramolybdate and 1.65 g of ammonium paratungstate were added into 150 ml of de-ionized water. The mixture was stirred and heated to 95° C. to form a solution.

A second solution was prepared by adding 10 ml of acetic acid to 20 ml of de-ionized water. 9.98 g of bismuth nitrate was dissolved in the acetic acid solution after which 10 ml of de-ionized water was added. To this solution was added 19.94 g of ferric nitrate, 23.92 nickel nitrate, 12.03 g of cobalt nitrate, 2.64 g of magnesium nitrate and 3.24 g of zinc nitrate with 10 ml of de-ionized water added after each addition of a nitrate compound.

The second solution was added to the first solution dropwise. Precipitates were formed during the addition which created a slurry.

2.41 g of cesium nitrate and 2.11 g of antimony oxide were added as solids to the slurry.

The slurry was aged for 10 hours at 80° C. while being stirred. After aging, the liquid was evaporated at 100° C. The solid was dried at 120° C. for 3 hours. The dried solid was calcined at 300° C. for 2 hours in flowing air. The calcined solid was sieved to a mesh size of 20–30. The sieved solid was calcined at 500° C. for 6 hours in flowing air. A catalyst of the following composition was obtained: $Mo_{12}Bi_{1.0}W_{0.3}Fe_{2.4}Co_{2.0}Ni_{4.0}Sb_{0.7}Cs_{0.6}Mg_{0.5}Zn_{0.5}$

EXAMPLE 2

The procedure of Example 1 was repeated except 20 ml of acetic acid was used.

EXAMPLE 3

The procedure of Example 1 was repeated except 20 ml of acetic acid was used and the calcination temperature was 480° C.

EXAMPLE 4

The procedure of Example 1 was repeated except 20 ml of acetic acid was used and the calcination temperature was 460° C.

EXAMPLE 5

The procedure of Example 1 was repeated except the calcination temperature was 480° C.

EXAMPLE 6

The procedure of Example 1 was repeated except the amount of ferric nitrate was 20.69 g and the amount of cesium nitrate was 2.50 g so that the composition of the catalyst was $Mo_{12}Bi_{1.0}W_{0.3}Fe_{2.5}Co_{2.0}Ni_{4.0}Sb_{0.7}Cs_{0.625}Mg_{0.5}Zn_{0.5}$

EXAMPLE 7

The procedure of Example 1 was repeated except the amount of ferric nitrate was 20.69 g and the amount of cesium nitrate was 2.50 g so that the composition of the catalyst was $Mo_{12}Bi_{1.0}W_{0.3}Fe_{2.5}Co_{2.0}Ni_{4.0}Sb_{0.7}Cs_{0.625}Mg_{0.5}Zn_{0.5}$ and the calcination temperature was 480° C.

EXAMPLE 8

The procedure of Example 1 was repeated except the amount of the amount of cesium nitrate was 2.02 g so that the composition of the catalyst was $Mo_{12}Bi_{1.0}W_{0.3}Fe_{2.4}Co_{2.0}Ni_{4.0}Sb_{0.7}Cs_{0.5}Mg_{0.5}Zn_{0.5}$

EXAMPLE 9

The procedure of Example 1 was repeated except the amount of the amount of cesium nitrate was 2.02 g so that the composition of the catalyst was $Mo_{12}Bi_{1.0}W_{0.3}Fe_{2.4}Co_{2.0}Ni_{4.0}Sb_{0.7}Cs_{0.5}Mg_{0.5}Zn_{0.5}$ and the calcination temperature was 480° C.

EXAMPLE 10

The procedure of Example 1 was repeated except the magnesium nitrate was eliminated so that the composition of the catalyst was $Mo_{12}Bi_{1.0}W_{0.3}Fe_{2.4}Co_{2.0}Ni_{4.0}Sb_{0.7}Cs_{0.6}Zn_{0.5}$

EXAMPLE 11

The procedure of Example 1 was repeated except the magnesium nitrate was eliminated so that the composition of the catalyst was $Mo_{12}Bi_{1.0}W_{0.3}Fe_{2.4}Co_{2.0}Ni_{4.0}Sb_{0.7}Cs_{0.6}Zn_{0.5}$ and the calcination temperature was 480° C.

EXAMPLE 12

The procedure of Example 1 was repeated except the amount of the bismuth nitrate was 5.09 g, the amount of ferric nitrate was 22.03 g and the amount of antimony oxide was 3.08 g so that the composition of the catalyst was $Mo_{12}Bi_{0.5}W_{0.3}Fe_{2.6}Co_{2.0}Ni_{4.0}Sb_{1.0}Cs_{0.6}Zn_{0.5}$

EXAMPLE 13

The procedure of Example 1 was repeated except 0.24 g of phosphoric acid (85%) was added to the solution of the ammonium paramolybdate and the ammonium paratungstate so that the composition of the catalyst was $Mo_{12}Bi_{0.5}W_{0.3}Fe_{2.6}Co_{2.0}Ni_{4.0}Sb_{1.0}Cs_{0.6}Zn_{0.5}P_{0.1}$.

EXAMPLE 14

The procedure of Example 1 was repeated except 0.24 g of phosphoric acid (85%) was added to the solution of the ammonium paramolybdate and the ammonium paratungstate so that the composition of the catalyst was $Mo_{12}Bi_{0.5}W_{0.3}Fe_{2.6}Co_{2.0}Ni_{4.0}Sb_{1.0}Cs_{0.6}Zn_{0.5}P_{0.1}$ and the calcination temperature was 480° C.

COMPARATIVE EXAMPLE 45.52 g of ammonium paramolybdate and 1.73 g of ammonium paratungstate were added into 150 ml of de-ionized water. The mixture was stirred and heated to 95° C. to form a solution.

A second solution was prepared by adding 1.3 g of 69% nitric acid to 9 ml of de-ionized water. 6.25 g of bismuth nitrate was dissolved in the nitric acid solution after which 10 ml of de-ionized water was added. To this solution was added 17.36 g of ferric nitrate, 24.99 nickel nitrate, 12.57 g of cobalt nitrate, 2.76 g of magnesium nitrate and 3.38 g of zinc nitrate after which 85 g of de-ionized water was added.

The second solution was added to the first solution dropwise. Precipitates were formed during the addition which created a slurry.

2.52 g of cesium nitrate and 2.21 g of antimony oxide were added as solids to the slurry.

The slurry was aged for 10 hours at 80° C. while being stirred. After aging, the liquid was evaporated at 100° C. The solid was dried at 120° C. for 3 hours. The dried solid was calcined at 300° C. for 2 hours in flowing air. The calcined solid was sieved to a mesh size of 20–30. The sieved solid was calcined at 500° C. for 6 hours in flowing air.

A catalyst of the following composition was obtained: 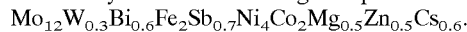

EXAMPLE 15

The procedure of the Comparative Example was repeated except 20 ml of acetic acid was used instead of nitric acid and 10 ml of de-ionized water was added after each addition of a nitrate compound (as in Example 1).

A catalyst of the following composition was obtained: 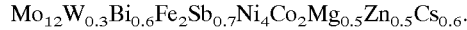

For each of the catalysts from the Examples above, 1.2–2.5 cc of catalyst were mixed with quartz chips to make a total volume of 5 cc which were placed into a downflow reactor having an internal diameter of 0.25 inches. A gas consisting of 3.9% isobutylene, 8.4% oxygen, 28% water and the balance as nitrogen was passed over the catalyst bed in the reactor. The volumetric flow rates were varied between 38 and 105 sccm. The internal reactor temperature was maintained at 390° C. The catalyst loading and gas flow rate were adjusted such that a conversion between 98 and 99% was obtained. Product liquid was condensed into a glass trap maintained at 0° C. for a period of approximately three hours. The yields of methacrylic acid and acetic acid were determined from this liquid. The concentrations of isobutylene, methacrolein and the byproducts were determined from on-line analysis by gas chromatography.

Catalyst activities are reported in Table I relative to the Comparative Example for which 1.5 cc of catalyst gave 97.7% conversion at 38 sccm flow rate, 89.1% selectivity and 87.0% one pass yield. The measurement error was roughly +/−7% for the activities. Selectivities adjusted for process conditions and specific conversion were the same for each catalyst within experimental error. The measurement error was roughly +/−1% for the selectivities. Mass balances were measured for every example and averaged 96%.

In all of the examples, adjustments were made for difference in conversion and space velocity, due to differences in amount of catalyst or gas flow rate, by assuming that the reaction is net first order in isobutylene concentration.

TABLE I

| EXAMPLE | ACID/AMOUNT | CALCINATION TEMPERATURE | RELATIVE ACTIVITY |
|---|---|---|---|
| 1 | AA/10 ml | 500° C. | 0.81 |
| 2 | AA/20 ml | 500° C. | 0.81 |
| 3 | AA/20 ml | 480° C. | 0.71 |
| 4 | AA/20 ml | 460° C. | 0.85 |
| 5 | AA/10 ml | 480° C. | 0.67 |
| 6 | AA/10 ml | 500° C. | 0.70 |
| 7 | AA/10 ml | 480° C. | 0.56 |

TABLE I-continued

| EXAMPLE | ACID/AMOUNT | CALCINATION TEMPERATURE | RELATIVE ACTIVITY |
|---|---|---|---|
| 8 | AA/10 ml | 500° C. | 0.78 |
| 9 | AA/10 ml | 480° C. | 1.02 |
| 10 | AA/10 ml | 500° C. | 0.98 |
| 11 | AA/10 ml | 480° C. | 1.27 |
| 12 | AA/10 ml | 500° C. | 0.54 |
| 13 | AA/10 ml | 500° C. | 1.20 |
| 14 | AA/10 ml | 480° C. | 1.41 |
| COMPARATIVE | NA/1.3 g | 500° C. | 1.00 |
| 15 | AA/20 ml | 500° C. | 1.26 |

AA - Acetic Acid
NA - Nitric Acid

The above examples demonstrate the effectiveness of acetic acid in the synthesis of a mixed metal oxide catalyst for the catalytic oxidation of an olefin to an unsaturated aldehyde, e.g., propylene or isobutylene to acrolein or methacrolein. Substitution of acetic acid for nitric acid to dissolve bismuth nitrate can increase catalyst activity (Example 15 v. Comparative Example). In addition, certain variables improve the performance of a catalyst which was synthesized with acetic acid as a solvent:

1. A lower amount of cesium and a lower calcination temperature (Example 9 v. Example 1).
2. The absence of magnesium (Example 10 v. Example 1).
3. The absence of magnesium and a lower calcination temperature (Example 11 v. Example 1).
4. The presence of phosphorus (Example 13 v. Example 1)
5. The presence of phosphorus and a lower calcination temperature (Example 14 v. Example 1)

Preferably, the amount of cesium is 0.4 to 0.6, the amount of magnesium is 0, the amount of phosphorus is 0.05 to 0.15 and the calcination temperature is 460° C. to 480° C.

Modifications and variations of the present invention in light of the above teachings are understood to be within the scope of the appended claims, and the invention may be practiced other than as specifically described therein.

What is claimed as new and desired to be secured by Letter of Patent of the United States of America is:

1. A process for preparing a catalyst for the oxidation of an olefin to an unsaturated aldehyde comprising:

a) dissolving a bismuth compound to form a solution or a slurry in an organic acid;

b) bringing the bismuth compound in contact with a molybdenum compound, an iron compound, and a cesium compound in the solution or slurry;

c) removing liquid from the solution or the slurry to form a solid;

d) drying the solid; and e) calcining the solid to form oxides of the metals to form a catalyst having the general formula:

wherein a is in the range from 0.1 to 1.5, c is in the range from 0.2 to 5.0, g is in the range from 0.1 to 1.5 and x is determined by the valences of the other components.

2. The process of claim 1 wherein the organic acid has the general formulae:

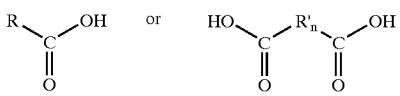

where R is an alkyl group of one to six carbon atoms, an aryl group of six to ten carbon atoms, an alkylhydroxy group of one to six carbon atoms or an alkylhalide group of one to six carbon atoms, R' is an alkyl group of one to six carbon atoms or an aryl group of six to ten carbon atoms and n is 1 or 0 indicating whether the R' group is present or not.

3. The process of claim 2 wherein the organic acid is acetic acid, formic acid, citric acid, oxalic acid, benzoic acid, phthalic acid, lactic acid, malonic acid, adipic acid or chloroacetic acid.

4. The process of claim 3 wherein the organic acid is acetic acid.

5. The process of claim 1 wherein the molybdenum compound is an ammonium salt.

6. The process of claim 1 further comprising bringing the bismuth compound in contact with a tungsten compound.

7. The process of claim 6 wherein the tungsten compound is an ammonium salt.

8. The process of claim 1 wherein the bismuth compound is a nitrate.

9. The process of claim 1 wherein the iron compound is a nitrate.

10. The process of claim 1 further comprising bringing the bismuth compound in contact with a cobalt compound.

11. The process of claim 10 wherein the cobalt compound is a nitrate.

12. The process of claim 1 further comprising bringing the bismuth compound in contact with a nickel compound.

13. The process of claim 12 wherein the nickel compound is a nitrate.

14. The process of claim 1 further comprising bringing the bismuth compound in contact with an antimony compound.

15. The process of claim 14 wherein the antimony compound is an oxide.

16. The process of claim 1 wherein the cesium compound is a nitrate.

17. The process of claim 1 further comprising bringing the bismuth compound in contact with a zinc compound.

18. The process of claim 17 wherein the zinc compound is a nitrate.

19. The process of claim 1 further comprising bringing the bismuth compound in contact with one or more compound of M wherein M is selected from the group consisting of tungsten, cobalt, nickel, antimony, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium and wherein the catalyst has a formula:

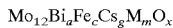

wherein m is 0 to 9.

20. The process of claim 19 wherein the catalyst has a formula:

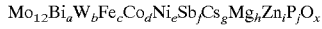

wherein a is 0.1 to 1.5, b is 0 to 4, c is 0.2 to 5.0, d is 0 to 9, e is 0 to 9, f is 0 to 2.0, g is 0.4 to 1.5, h is 0 to 1.5, i is 0 to 2.0, j is 0 to 0.5.

21. The process of claim 20 wherein the bismuth compound, the iron compound, the cobalt compound, the nickel compound, the magnesium compound and the zinc compound are dissolved in an organic acid to form a solution.

22. The process of claim 21 wherein the solution containing the bismuth compound, the iron compound, the cobalt compound, the nickel compound, the magnesium compound and the zinc compound are mixed with the solution containing the molybdenum compound, the tungsten compound and the phosphorus compound to form a slurry.

23. The process of claim 22 wherein the cesium compound is added as a solid to the slurry.

24. The process of claim 23 wherein the antimony compound is added as a solid to the slurry.

25. The process of claim 24 wherein the slurry is aged for 0 to 24 hours.

26. The process of claim 25 wherein the slurry is aged for 8 to 18 hours.

27. The process of claim 26 wherein the slurry is aged for 10 hours.

28. The process of claim 25 wherein the slurry is stirred during aging.

29. The process of claim 25 wherein the slurry is maintained at a temperature of 60 to 100° C. during aging.

30. The process of claim 20 wherein the catalyst has an X-ray diffraction pattern having substantial diffraction peaks at the diffraction angles of 2θ, measured by using Cu Kα radiation, at 25.5, 26.6 and 28.0.

31. The process of claim 20 wherein the catalyst is unsupported and has a surface area of from 0.1 to 150 m²/g.

32. The process of claim 31 wherein the catalyst has a surface area of from 1 to 20 m²/g.

33. The process of claim 19 wherein the molybdenum compound, the tungsten compound and the phosphorus compound are dissolved in water to form a solution.

34. The process of claim 1 wherein the liquid is removed by evaporation at a temperature of 75 to 125° C.

35. The process of claim 1 wherein the liquid is removed by filtration.

36. The process of claim 1 wherein the liquid is removed by centrifuge.

37. The process of claim 1 wherein the liquid is removed and the solid dried by spray drying.

38. The process of claim 1 wherein the solid is dried 100° to 150° C. for 2 to 5 hours.

39. The process of claim 1 wherein the solid is calcined at 200–600° C. for 1–12 hours.

40. The process of claim 39 wherein the solid is calcined in two stages, the first stage at a temperature of 150–400° C. for 1–5 hours and the second state at a temperature of 460–600° C. for 4–8 hours.

41. The process of claim 40 wherein the solid is calcined in the first stage at a temperature of 300° C. for 2 hours and in second stage at a temperature of 500° C. for 6 hours.

42. The process of claim 1 wherein the catalyst is supported on an inert support.

43. The process of claim 42 wherein the inert support is silica, alumina, niobia, titania, zirconia or mixtures thereof.

44. The process of claim 1 wherein the catalyst is formed into powder, granules, spheres, cylinders or saddles.

45. A process for preparing a catalyst for the oxidation of isobutylene to methacrolein comprising:
   a) dissolving bismuth nitrate to form a solution or a slurry in acetic acid;
   b) bringing the bismuth nitrate in contact with a molybdenum compound selected from the group consisting of ammonium paramolybdate and ammonium molybdate, a tungsten compound selected from the group consisting of ammonium paratungstate and ammonium tungstate, iron nitrate, cobalt nitrate, nickel nitrate, cesium nitrate, magnesium nitrate, zinc nitrate, phosphoric acid and an antimony compound selected from the group consisting of antimony oxide and antimony trioxide;

c) removing liquid from the solution or the slurry to form a solid;

d) drying the solid; and e) calcining the solid at a temperature to form oxides of the metals to form a catalyst having the general formula

$Mo_{12}Bi_aW_bFe_cCo_dNi_eSb_fCs_gMg_hZn_iP_jO_x$ wherein a is 0.1 to 1.5, b is 0 to 4, c is 0.2 to 5.0, d is 0 to 9, e is 0 to 9, f is 0 to 2.0, g is 0.4 to 1.5, h is 0 to 1.5, i is 0 to 2.0, j is 0 to 0.5.

46. The process of claim 45 wherein g is 0.4 to 0.6 and the calcination temperature is 460° C. to 480° C.

47. The process of claim 45 wherein h is 0.

48. The process of claim 47 wherein the calcination temperature is 460° C. to 480° C.

49. The process of claim 45 wherein j is 0.05 to 0.15.

50. The process of claim 49 wherein the calcination temperature is 460° C. to 480°.

* * * * *